US008870939B2

(12) United States Patent
Roeder et al.

(10) Patent No.: US 8,870,939 B2
(45) Date of Patent: Oct. 28, 2014

(54) PROSTHESIS HAVING PIVOTING FENESTRATION

(71) Applicant: Cook Medical Technologies LLC, Bloomington, IN (US)

(72) Inventors: Blayne A. Roeder, Lafayette, IN (US); Matthew S. Huser, West Lafayette, IN (US); David E. Hartley, Wannanup Western Australia (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/729,933

(22) Filed: Dec. 28, 2012

(65) Prior Publication Data
US 2013/0116775 A1    May 9, 2013

Related U.S. Application Data

(63) Continuation-in-part of application No. 13/213,349, filed on Aug. 19, 2011.

(60) Provisional application No. 61/375,815, filed on Aug. 21, 2010.

(51) Int. Cl.
| *A61F 2/06* | (2013.01) |
| *A61F 2/82* | (2013.01) |
| *A61F 2/07* | (2013.01) |
| *A61F 2/856* | (2013.01) |
| *A61F 2/89* | (2013.01) |

(52) U.S. Cl.
CPC ......... *A61F 2/856* (2013.01); *A61F 2230/0054* (2013.01); *A61F 2220/005* (2013.01); *A61F 2002/821* (2013.01); *A61F 2/07* (2013.01); *A61F 2002/075* (2013.01); *A61F 2220/0075* (2013.01); *A61F 2230/0067* (2013.01); *A61F 2002/061* (2013.01); *A61F 2230/005* (2013.01); *A61F 2/89* (2013.01)
USPC .................. 623/1.13; 623/1.31; 623/1.37

(58) Field of Classification Search
USPC ........................................ 623/1.13
See application file for complete search history.

(56) References Cited

U.S. PATENT DOCUMENTS

| 1,597,525 A | 8/1926 | Knake |
| 5,366,473 A | 11/1994 | Winston et al. |

(Continued)

FOREIGN PATENT DOCUMENTS

| EP | 1673039 | 6/2006 |
| EP | 1847234 | 10/2007 |

(Continued)

OTHER PUBLICATIONS

Branched and Fenestrated Stent-Grafts presentation, Tim Chuter, MD, 15 pages.

(Continued)

*Primary Examiner* — Thomas J Sweet
*Assistant Examiner* — Tiffany Shipmon
(74) *Attorney, Agent, or Firm* — Brinks Gilson & Lione

(57) ABSTRACT

The present disclosure relates to an endoluminal prosthesis, such as a stent graft that includes one or more fenestrations to accommodate endovascular disease, such as an aneurysm in cases where one or more side branches is involved. In one aspect, the prosthesis includes fenestrations that are pivotable to accommodate the dynamic geometry of the aortic branches. In another aspect, the pivotable fenestrations include a first perimeter, a band of flexible material attached and surrounding the first perimeter, and a second perimeter attached to and surrounding the band of flexible material. The first perimeter, band of flexible material, and second perimeter have a geometric shape. In one aspect, the prosthesis includes at least three pivotable fenestrations.

22 Claims, 10 Drawing Sheets

(56) References Cited

U.S. PATENT DOCUMENTS

| | | | |
|---|---|---|---|
| 5,425,765 | A | 6/1995 | Tiefenbrun et al. |
| 5,445,600 | A | 8/1995 | Abdulla |
| 5,603,698 | A | 2/1997 | Roberts et al. |
| 5,653,743 | A | 8/1997 | Martin |
| 5,662,703 | A | 9/1997 | Yurek et al. |
| 5,676,697 | A | 10/1997 | McDonald |
| 5,984,955 | A | 11/1999 | Wisselink |
| 6,086,526 | A | 7/2000 | Francischelli |
| 6,344,052 | B1 | 2/2002 | Greenan et al. |
| 6,395,018 | B1 | 5/2002 | Castaneda |
| 6,514,286 | B1 | 2/2003 | Leatherbury et al. |
| 6,524,335 | B1 | 2/2003 | Hartley et al. |
| 6,942,879 | B2 | 9/2005 | Humes |
| 7,678,141 | B2 | 3/2010 | Greenan et al. |
| 2002/0052648 | A1 | 5/2002 | McGuckin, Jr. et al. |
| 2002/0058992 | A1 | 5/2002 | Greenhalgh |
| 2002/0198585 | A1 | 12/2002 | Wisselink |
| 2003/0199967 | A1 | 10/2003 | Hartley et al. |
| 2004/0034406 | A1 | 2/2004 | Thramann |
| 2004/0059406 | A1 | 3/2004 | Cully et al. |
| 2004/0106972 | A1 | 6/2004 | Deaton |
| 2004/0215327 | A1 | 10/2004 | Doig et al. |
| 2005/0102021 | A1 | 5/2005 | Osborne |
| 2005/0131517 | A1 | 6/2005 | Hartley et al. |
| 2005/0131518 | A1* | 6/2005 | Hartley et al. ............ 623/1.13 |
| 2005/0149166 | A1 | 7/2005 | Schaeffer et al. |
| 2005/0171597 | A1 | 8/2005 | Boatman et al. |
| 2005/0171598 | A1 | 8/2005 | Schaeffer |
| 2005/0182476 | A1 | 8/2005 | Hartley et al. |
| 2005/0222668 | A1 | 10/2005 | Schaeffer et al. |
| 2005/0222669 | A1 | 10/2005 | Purdy |
| 2005/0228488 | A1 | 10/2005 | Nazzaro |
| 2005/0273155 | A1 | 12/2005 | Bahler et al. |
| 2006/0058864 | A1 | 3/2006 | Schaeffer et al. |
| 2006/0247760 | A1 | 11/2006 | Ganesan et al. |
| 2007/0244547 | A1 | 10/2007 | Greenan |
| 2007/0276468 | A1 | 11/2007 | Holzer et al. |
| 2009/0030502 | A1 | 1/2009 | Sun et al. |
| 2009/0164001 | A1 | 6/2009 | Biggs et al. |
| 2009/0240316 | A1 | 9/2009 | Bruszewski |
| 2009/0259290 | A1 | 10/2009 | Bruszewski et al. |
| 2009/0264821 | A1 | 10/2009 | Mafi et al. |
| 2009/0264991 | A1 | 10/2009 | Paul et al. |
| 2010/0063576 | A1 | 3/2010 | Schaeffer et al. |
| 2010/0268319 | A1* | 10/2010 | Bruszewski et al. ......... 623/1.13 |
| 2010/0268327 | A1 | 10/2010 | Bruszewski et al. |
| 2011/0054586 | A1 | 3/2011 | Mayberry et al. |
| 2011/0166644 | A1 | 7/2011 | Keeble et al. |
| 2012/0221096 | A1 | 8/2012 | Roeder et al. |

FOREIGN PATENT DOCUMENTS

| | | |
|---|---|---|
| WO | 2005/034810 | 4/2005 |
| WO | 2009/056644 | 5/2009 |
| WO | 2010/127040 | 11/2010 |
| WO | 2011/136940 | 11/2011 |

OTHER PUBLICATIONS

Branched Stent-Grafts presentation, Tim Chuter, MD, 24 pages.

Branched Stent-Grafts presentation, Tim Chuter, MD, 2002, 30 pages.

Branched Stent-Grafts presentation, Tim Chuter, MD, 29 pages.

Endovascular AAA Repair presentation, Tim Chuter, MD, 2002, 56 pages.

Endovascular AAA Repair presentation, Tim Chuter, MD, 2002, 44 pages.

Endovascular AAA Repair presentation, Tim Chuter, MD, Division of Vascular Surgery, University of California San Francisco, updated Sep. 2002, Part 1-50 pgs and Part 2-44pgs.

Extended European Search Report, EU App. No. 11178162.1, Jul. 17, 2012, 8pp.

International Search Report completed May 8, 2013, PCT/US2013/027614, Feb. 25, 2013.

Extended European Search Report, EU App. No. 13275329, Apr. 29, 2014, 7pp.

* cited by examiner

PROSTHESIS HAVING PIVOTING FENESTRATION

RELATED APPLICATIONS

The present application is a continuation-in-part application that claims priority to U.S. Utility patent application Ser. No. 13/213,349, filed Aug. 19, 2011 and entitled "Prosthesis Having Pivoting Fenestration", which claims priority to U.S. Provisional Patent Application Ser. No. 61/375,815 filed Aug. 21, 2010, each of which are incorporated by reference in their entirety.

BACKGROUND OF THE INVENTION

The functional vessels of human and animal bodies, such as blood vessels and ducts, occasionally weaken or even rupture. For example, the aortic wall can weaken, resulting in an aneurysm, or it may develop a tear in one of the layers of the aortic wall resulting in an aortic dissection.

One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules. They also may be a single tubular device or a bifurcated branching device depending on the desired application.

In many cases, however, the damaged or defected portion of the vasculature may include a branch vessel branching from the main vessel. For example, in the case of the abdominal aorta, there are at least three major branch vessels, including the celiac, mesenteric, and renal arteries, as well as others, leading to various other body organs. Thus, when the damaged portion of the vessel includes one or more of these branch vessels, some accommodation must be made to ensure that the prosthesis does not block or hinder blood flow through the branch vessel. In many instances, there may be insufficient healthy tissue in the aorta near the branching vessels to adequately seal a prosthesis without partially or completely blocking one or more of the branching vessels.

SUMMARY

The present disclosure relates to an endoluminal prosthesis, such as a stent graft that includes one or more fenestrations to accommodate endovascular disease, such as an aneurysm in cases where one or more side branches is involved. In one aspect, the prosthesis includes fenestrations that are pivotable to accommodate the dynamic geometry of the aortic branches. The use of pivotable fenestrations also allows the design of a family of standard stent grafts for "off-the-shelf" use to accommodate a majority of aneurysm cases involving side branches and reducing the need for customization in many cases.

In one aspect, a prosthesis includes one or more pivotable fenestrations that accommodate the variability associated with patient anatomy, both statically and dynamically. For example, one or more pivotable fenestrations provided on a prosthesis may lie outside the surface plane of the body of the prosthesis and will allow a branch vessel stent, graft or stent-graft that has been placed in the fenestration to pivot into any orientation required to meet and seal the branch vessel device in the branch vessel. In some aspects, the prosthesis may be useful for treating Type IV thoracoabdominal aortic aneurysms that involve all four visceral branch arteries (celiac, superior mesenteric artery, and the renal arteries), where the disease expands above the superior mesenteric artery. The prosthesis may include a stent frame having a plurality of stent units attached to the graft about the surface of the graft and arranged in longitudinally spaced rows, at least one of the stent units comprising a plurality of struts interconnected by apices.

The pivotable fenestrations may include an inner perimeter surrounding the fenestration (the hole) in the graft, a band of material surrounding the inner perimeter and extending radially outwardly of the surface plane of the prosthesis, and an outer perimeter surrounding the band of material where the band joins the surface of the prosthesis. The band of material extending from the surface of the prosthesis is sufficiently flexible to permit the fenestration to move such that a branch stent disposed in the fenestration may be oriented upwardly, downwardly, laterally, diagonally and the like. Further, the pivotable fenestration may independently move from an interior surface of the prosthesis to an exterior surface of the prosthesis while the prosthesis is being deployed in a vessel. In addition, the fenestration may be oriented inwardly or outwardly of the surface of the prosthesis. Hence, a device of a single geometry may accommodate a variety of patient anatomies. In a further aspect, the inner perimeter, the band of material, and the outer perimeter may have a geometric shape. In another aspect, the first perimeter of at least one of the fenestrations has a diameter of about 8 mm. In still another aspect, at least one of the pivotable fenestrations is configured to be positioned proximate the celiac artery. In another aspect, at least one of the pivotable fenestrations is configured to be positioned proximate the superior mesenteric artery. The pivotable fenestrations may include a frame attached to and surrounding the second perimeter. In another aspect, the band of material is integral with the sidewall of the graft. In another aspect, the band of material is separately attached to the surface of the graft.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION

Figure 1:
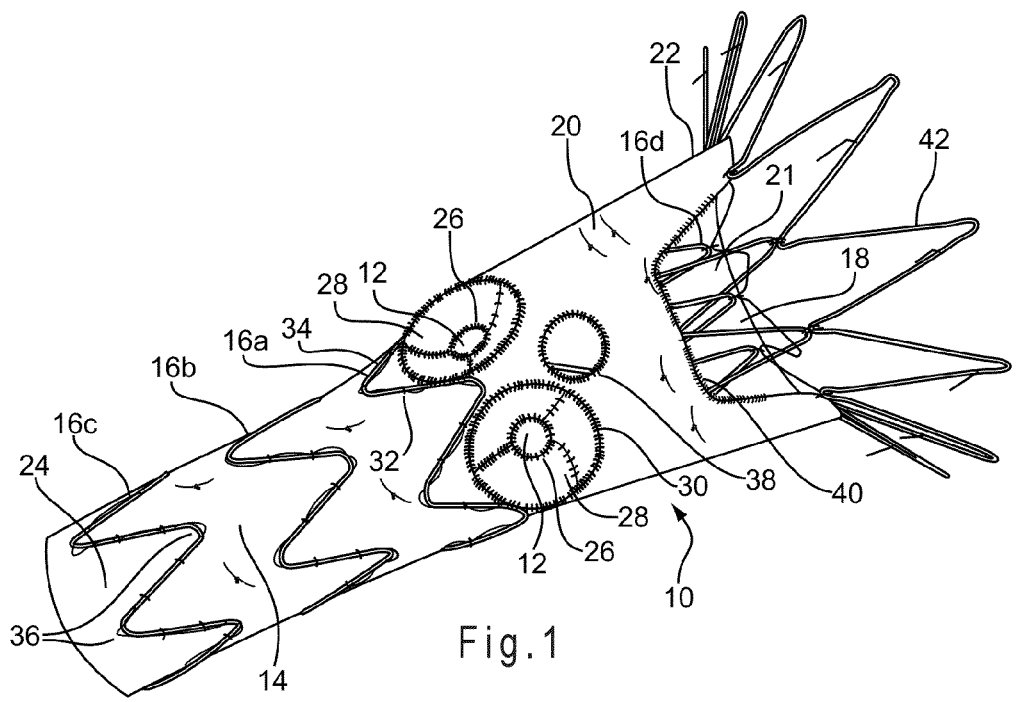
FIG. 1 shows a perspective view of a fenestrated prosthesis having concave (internal) pivotable fenestrations.

The present disclosure relates to an endoluminal prosthesis, such as a stent graft that includes one or more fenestrations to accommodate endovascular disease, such as an aneurysm in cases where one or more side branches is involved, and a side branch prosthesis is deployed within the fenestration to permit fluid flow from the endoluminal prosthesis into the branch vessel. The prosthesis includes fenestrations that pivot as needed to accommodate the dynamic geometry of the aortic branches. In various aspects shown and described in more detail below, for example, one or more pivotable fenestrations provided on a prosthesis lie outside the surface plane of the body of the prosthesis and will allow a branch vessel stent, graft or stent-graft that has been placed in the fenestration to pivot into a variety of orientations required to meet and seal the branch vessel device in the branch vessel. The orientation of the fenestrations may dynamically change over time as needed by changing anatomy.

DEFINITIONS

Unless defined otherwise, all technical and scientific terms used herein have the same meaning as commonly understood to one of ordinary skill in the art to which this invention belongs.

The term "distal" means a location or direction that is, or a portion of a device that when implanted is further downstream in the direction of or with respect to blood flow.

The term "proximal" means a location or direction that is, or a portion of a device that when implanted is further upstream in the direction of or with respect to blood flow.

The term "fenestration" means an opening provided through a surface of a prosthesis from the interior of the prosthesis to the exterior of the prosthesis and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate, fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the material's surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompass any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may be constructed from natural or organic materials, for example and without limitation, a biological scaffold or bioremodelable material, such as small intestine submucosa ("SIS"), which is commercially available by Cook Biotech, West Lafayette, Ind. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent." The stents may be comprised of a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as nitinol, or other suitable materials as known in the art. The stents may be made of a wire, or may be laser or cannula cut, or manufactured by other known methods.

The term "yarn" refers to a length of a continuous thread or strand of one or more filaments or fibers, with or without twist, suitable for weaving, knitting or otherwise intertwining to form a textile fabric.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

"Longitudinally" refers to a direction, position or length substantially parallel with a longitudinal axis of a reference, and is the length-wise component of the helical orientation.

"Circumferentially" refers to a direction, position, or length that encircles a longitudinal axis of a reference. The term "circumferential" is not restricted to a full 360° circumferential turn or to a constant radius.

The terms "patient," "subject," and "recipient" as used in this application refer to any animal, especially humans.

FIGS. 1-8 show a fenestrated prosthesis 10, here a stent graft, having a tubular body and comprising a biocompatible material, having one or more fenestrations 12 pivotable in any direction away from an axis perpendicular to a longitudinal axis of the prosthesis. The pivotable fenestrations 12 have a diameter extending from a sidewall of the graft. The pivotable fenestrations 12 include a first, inner perimeter 26 surrounding the fenestration 12 having a diameter, a band 28 of flexible material attached to and surrounding the first perimeter 26, and a second, outer perimeter 30 attached to and surrounding the band 28 of flexible material. The band 28 of material has a first diameter that is substantially the same as the diameter of the first perimeter 26, and a second diameter substantially the same as the second perimeter 30. The diameter of the band of material decreases in a direction away from the surface 20 of the graft 14 from the second perimeter to the first perimeter. The band of flexible material may include a flexible frame 48.

In some aspects, the fenestrated prosthesis 10 is intended for placement in the abdominal aorta and to accommodate vessels that branch from the aorta, for example, the renal arteries, and into which a branch vessel prosthesis may be placed. However, the fenestrated prosthesis 10 is not limited for use in the abdominal aorta but may be used in other vessels of the body from which other vessels branch, such as the ascending thoracic aorta, the descending thoracic aorta, as well as other body vessels.

FIG. 1 shows a perspective view of a prosthesis 10 that is a stent graft. The prosthesis 10 includes graft material 14 associated with one or more stents 16. The prosthesis 10 has a proximal end 22, a distal end 24, and a lumen 18 extending through the prosthesis 10 to permit passage of blood flow from the proximal end 22 to the distal end 24. The stents 16 may be placed on the external surface 20 and/or internal surface 21 of the graft material 14. In one particular embodiment, the prosthesis 10, such as that shown in FIG. 1, has external body stents 16a, 16b, and 16c, and at least one internal stent 16d. The internal stent 16d may be a sealing stent and placed at or near the proximal end 22 of the prosthesis 10 to seal the prosthesis 10 at the proximal end 22 to the walls of a blood vessel into which it has been placed. Additionally, or alternatively, depending on the location of the prosthesis 10 or a particular need, a sealing stent 16d may be placed at either or both the proximal and distal ends 22, 24 of prosthesis 10. The prosthesis 10 also may include an attachment mechanism, for example, an attachment stent 42, at either or both ends of the prosthesis 10, to further secure the prosthesis 10 within the body vessel and prevent migration of the prosthesis 10.

As shown in FIG. 1, the prosthesis 10 has several openings or fenestrations that extend from the internal surface 21 to the external surface 20 of the graft material 14. The prosthesis 10 of FIG. 1 has two pivotable fenestrations 12, at least one non-pivotable fenestration 38, and a scallop 40. Here, the scallop 40 is placed at the proximal end 22 of the prosthesis 10.

FIGS. 1-8 show various aspects and views of the prosthesis 10 having pivotable fenestrations 12. Pivotable fenestrations 12 have an inner perimeter 26 surrounding the fenestration 12, a band 28 surrounding the inner perimeter 26, and an outer perimeter 30 surrounding the band 28. As shown, the outer perimeter 30 diameter is greater than the band 28 diameter and the inner perimeter diameter 26. The inner perimeter 26, the band 28 and the outer perimeter 30 would be substantially concentric with one another if they were in the same plane, for example the surface plane of the graft. The inner perimeter 26, the band 28 and the outer perimeter 30 may form a hemispherical shape, resembling a dome, or a frustoconical cone extending from the surface of the graft material 14. The fenestration 12 is provided at the peak or top of the hemispherical shape or extension. In other embodiments, the band 28 may comprise a tapered, flexible tube extending from the outer perimeter 30 and the inner diameter 26.

Stents 16, for example those shown in the Figures may be, for example zig zag stents, also known has Z-stents, that comprise a series of struts 32, 34 connected by apices 36, although the type of stent used is not so limited. When Z-stents are used, a portion of the outer perimeter 30 of one or more of the fenestrations 12 may lie between adjacent struts 32, 34 of one of the stents 16. The stents 16 may be either self-expanding or balloon expandable. Preferably, they are self-expanding. However, a combination of self-expanding and balloon expandable stents also may be contemplated.

Figure 5:
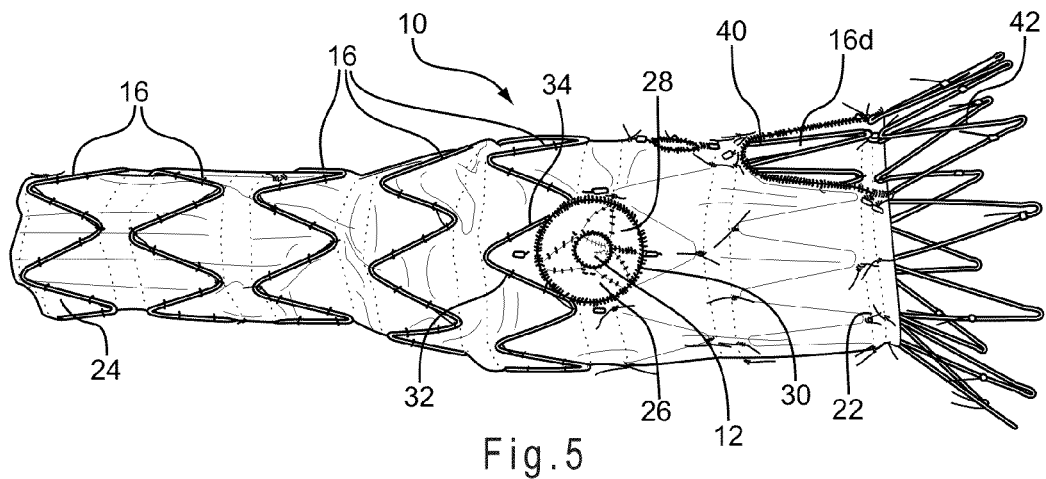
FIG. 5 shows another fenestrated prosthesis having concave (internal) pivotable fenestrations.

As set forth above, the stents 16 include struts 32, 34 that are spaced apart from each other. The strut spacing is measured from bend-to-bend (or apex to apex 36). Stent amplitude, spacing and stagger are preferably optimized for each prosthesis design. In some aspects, the apices or bends 36 of the struts 32, 34 may be staggered for minimal contact with each other. As shown in FIG. 1, the stents 16a, 16b, 16c are positioned adjacent each other and the apices 36 of each row are in circumferential alignment with the bends of longitudinally adjacent rows. In other aspects, as shown in FIG. 5, every bend 36 of each row may be in substantial circumferential alignment with the bends 36 of longitudinally adjacent rows.

The pivotable fenestrations 12 may be located within the lumen 18 of the prosthesis 10 or extending from the exterior of the prosthesis 10. In the first aspect, the pivotable fenestrations 12 may be said to be concave, relative to the external surface 20 of the graft material 14. In the second aspect, the pivotable fenestrations 12 may be said to be convex, relative to the external surface 20 of the graft material 14. FIG. 1 shows the pivotable fenestrations 12 located internal to the prosthesis 10, that is, they lie within the lumen 18 of the prosthesis 10. In the particular aspect shown in FIG. 1, the pivotable fenestrations 12 reside substantially on one side of the prosthesis 10 and are adjacent to one another. In the aspects shown in FIGS. 3-4 and 7-8, the pivotable fenestrations 12 are positioned to align with, for example, the renal arteries. In other aspects, the one or more pivotable fenestrations 12 may be positioned to align with other branch arteries throughout a diseased vasculature. Additional fenestrations and scallops as disclosed here may also be included.

Figure 2:
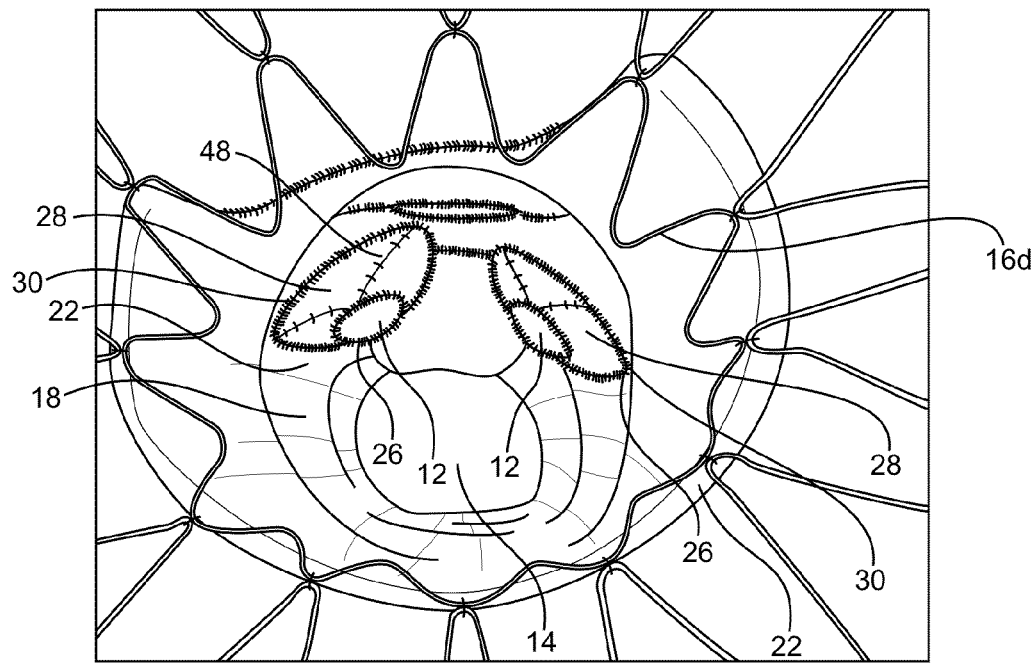
FIG. 2 is a partial and internal view of the prosthesis of FIG. 1.

FIG. 2, which is a partial internal view of the prosthesis 10 of FIG. 1, shows a view of the prosthesis 10 looking into the lumen 18 of the prosthesis 10 from the proximal end 22. As shown, pivotable fenestrations 12 extend or protrude into the lumen 18. Pivotable fenestrations 12 have an inner perimeter 26, a band 28, and an outer perimeter 30. As shown in FIG. 2, the outer perimeter 30 lies substantially flush (in the same plane) with the graft material 14, and the band 28 and the outer perimeter 30 form a hemispherical shape, such as a dome or frustoconical cone extending into the lumen 18. Although both the inner and outer perimeters 26, 30 are shown as substantially circular, they may be oval, oblong or some other desired geometric shape.

Figure 3:
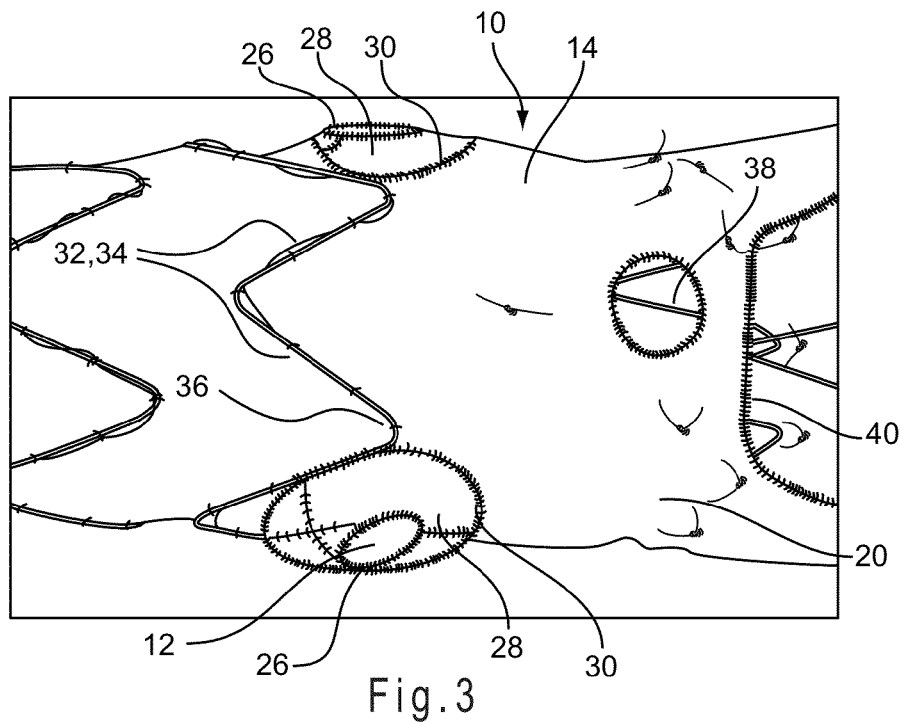
FIG. 3 shows a perspective view of a fenestrated prosthesis having convex (external) pivotable fenestrations.
Figure 4:
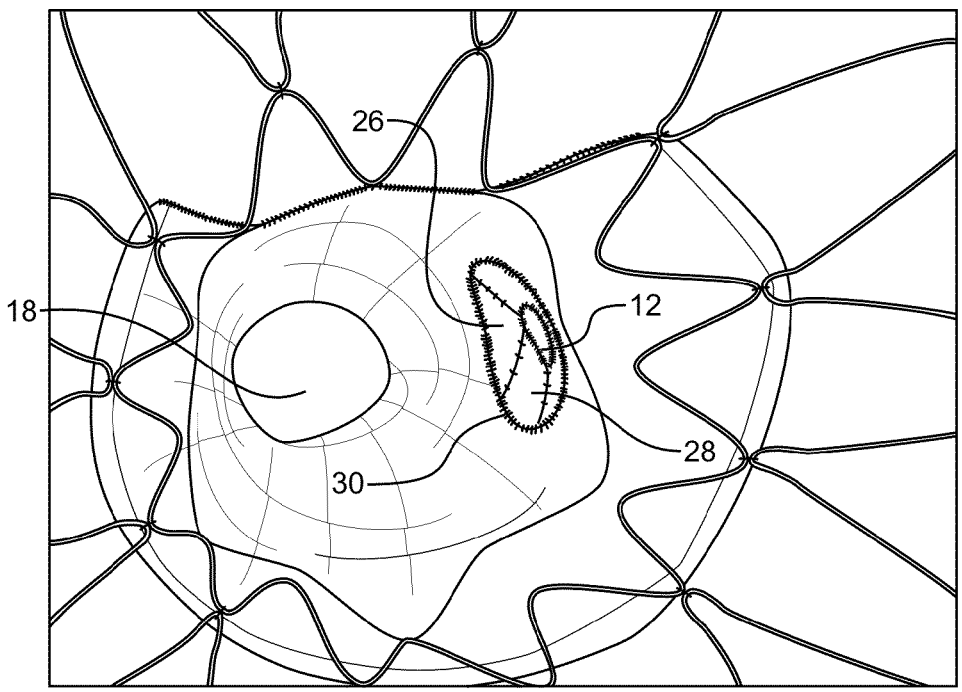
FIG. 4 is a partial and internal view of the prosthesis of FIG. 3.

FIGS. 3 and 4 show an aspect of a prosthesis 10 having externally extending pivotable fenestrations 12. FIG. 3 shows a partial view of a prosthesis 10 having two externally extending pivotable fenestrations 12 extending from opposite sides of the prosthesis 10. As with the other aspects, the fenestrations 12 have an inner perimeter 26 surrounding the fenestration, a band 28 of material surrounding the inner perimeter 26, and an outer perimeter 30 surrounding the band 28 of material. FIG. 4, which is a partial internal view of the prosthesis 10 of FIG. 3, shows a view of the prosthesis 10 of FIG. 3, looking into the lumen 18 of the prosthesis 10 from the proximal end 22. As shown, pivotable fenestrations 12 extend or protrude away from the external surface 20 of the graft material 14. The outer perimeter 30 lies substantially flush (in the same plane) with the graft material 14, and the band 28 and the outer perimeter 30 form a hemispherical shape, such as a dome, or frustoconical cone extending into the lumen 18.

Figure 6:
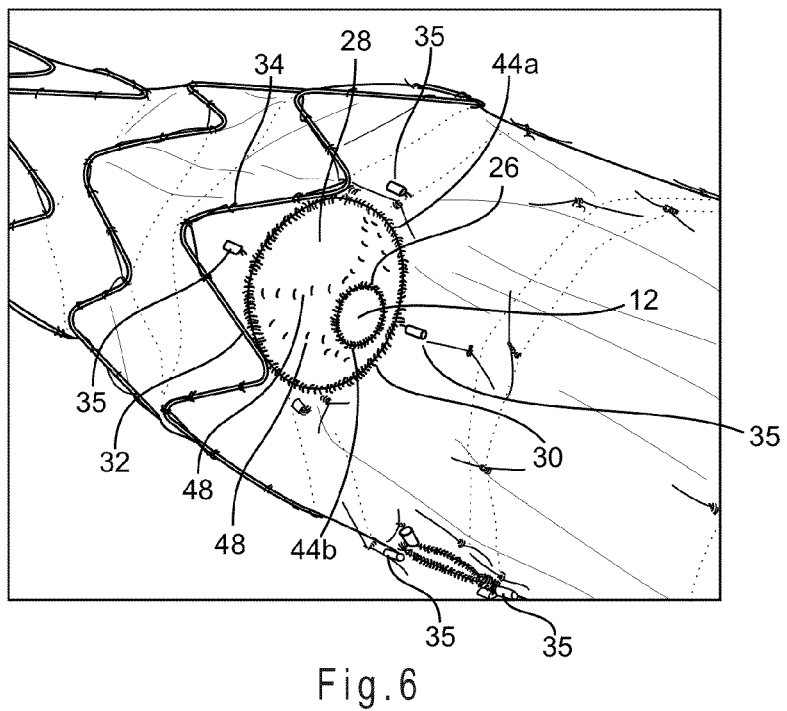
FIG. 6 is an enlarged perspective view of the pivotable fenestration shown FIG. 5.

FIGS. 5 and 6 show further aspects of a fenestrated prosthesis 10 having at least one pivotable fenestration 12. FIG. 5 shows a prosthesis 10 that is a stent graft. The prosthesis includes a proximal end 22, a distal end 24, a graft material 14 associated with a series of external stents 16. The prosthesis 10 further has an internal sealing stent 16d, and attachment stent 42, and a pivotable fenestration 12. FIG. 6 shows a partial close up view of the fenestration of FIG. 5. The pivotable fenestration 12 shown is an external fenestration 12 and has an inner perimeter 26 surrounding the fenestration 12, a band 28 of material surrounding the inner perimeter 26, and an outer perimeter 30 surrounding the band 28. As shown, a portion of the outer perimeter 30 lies between struts 32, 34 of the proximal most stent 16. Referring back to FIG. 5, the prosthesis 10 includes a non-pivoting fenestration 38 and a scallop 40 at the proximal end 22. As shown in these Figures and throughout the Figures, imageable markers 35, which may be viewed during and after placement of the prosthesis 10 may be placed at various locations on the prosthesis 10 to identify certain aspects of the prosthesis and their location during the implantation procedure and facilitate correct placement of the fenestrations 12, 38, scallop 40, the ends of the prosthesis and the like. For example, as shown in FIG. 6, markers 35 may be placed about the circumference of the outer perimeter 30. The markers 35 may be, for example, sewn or sutured to the graft material 14, as shown, or may be woven into the graft (not shown). The markers 35 also may be placed on the struts of one or more stents, for example, radiopaque marker tubes may be placed about one or more struts of the stent to indicate various areas of the stent graft. As shown, the markers 35 may be gold, however, any material that may be imaged by way of angiography, fluoroscopy, 3D imaging, MRI, or the like, may be suitable.

Figure 7:
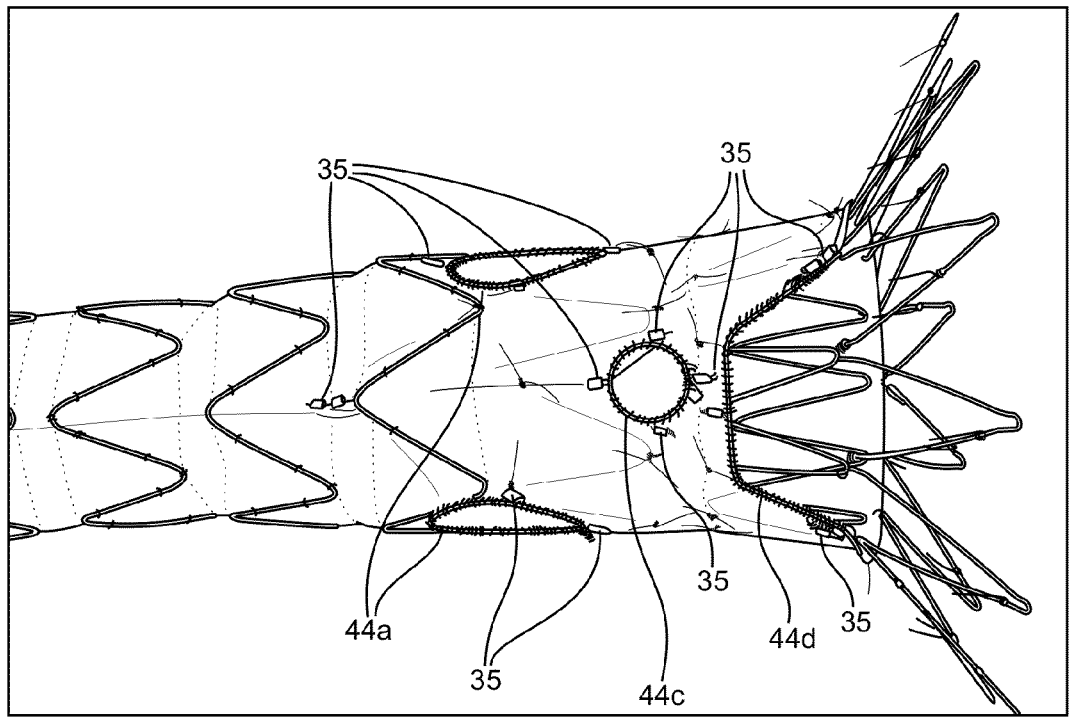
FIG. 7 shows a fenestrated prosthesis having imageable markers and reinforcement frames.

As further shown, particularly in FIGS. 6-7, the fenestrations 12, 38 and the scallop 40 may include a reinforcement frame 44a, 44b, 44c, 44d which may be sutured or otherwise attached to the graft 14. For example, in FIGS. 6-7, a reinforcement frame 44a may be positioned about the outer perimeter 30. As shown in FIG. 6, a reinforcement frame 44b may be positioned about the inner perimeter 26. As shown in FIG. 7, in particular, a reinforcement frame 44c may be provided about the non-pivoting fenestration 38, and reinforcement frame 44d may be provided about the perimeter of the scallop 40. The reinforcement frames 44a, 44b, 44c, 44d may be rings. In one preferred aspect, the reinforcement frames 44a, 44b, 44c, 44d are a wire that is sutured about the fenestration 12, 38, or scallop 40, to reinforce the fenestration or scallop. The reinforcement frames 44a, 44b, 44c, 44d may be made of any suitable material. One preferred material is a superelastic or shape memory material, such as nitinol. In another preferred embodiment, the reinforcement frames 44a, 44b, 44c, 44d may be made of radiopaque or other imageable material. In another embodiment the reinforcement frames 44a, 44b, 44c, 44d may be solid rings, or may be a wire that is looped about itself into a ring with unattached ends such that the ring may be expanded or contracted in diameter. Suitable frames are disclosed in U.S. patent application Ser. No. 10/962,632, filed Oct. 12, 2004, hereby incorporated by reference.

Figure 8:
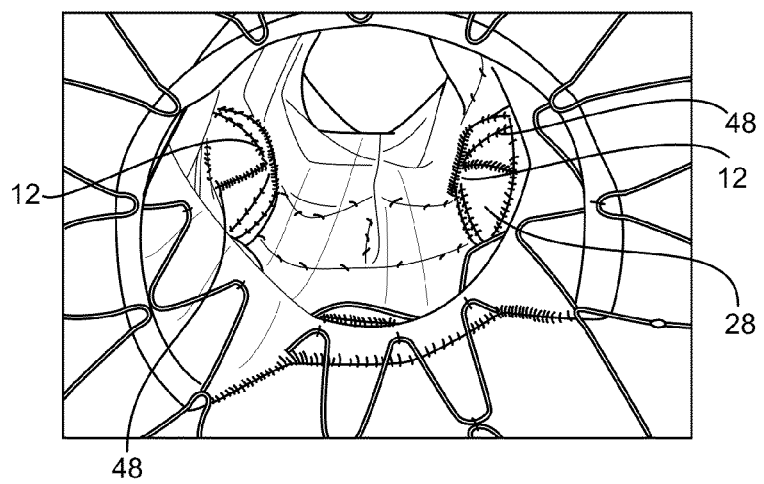
FIG. 8 is another partial and internal view of an internal pivotable fenestration.

FIG. 8 is another partial and internal view of a fenestrated prosthesis 10 having two internal pivotable fenestrations 12. As shown in this aspect, a dome-like projection or frustoconical extension is formed within the prosthesis 10. A flexible frame 48 may be disposed about or within the band 28.

As shown throughout the Figures, inner perimeter 26, band 28, and outer perimeter 30 surround the pivotable fenestration 12 to create a hemisphere shaped or frustoconical extension or protrusion. The outer perimeter 30 may be affixed to the graft material 14 by any attachment method including suturing circumferentially about an aperture disposed through graft material 14. The band 28 may be comprised of the same or different biocompatible material as the graft material 14. For example, the second biocompatible material may have greater pliability than the first biocompatible graft material used for the tubular graft body.

The band 28 is sufficiently flexible to permit the fenestration 12 to move such that a branch stent disposed in the fenestration 12 may be oriented upwardly, downwardly, laterally, diagonally and the like. In some aspects, the band has up to about 180 degrees of freedom of movement relative to the surface plane of the prosthesis 10. Accordingly, the pivotable fenestration 12 allows the prosthesis 10 to be used with a variety of patients, due to its ability to adapt to the variance in the positioning of the diseased branch vessels. For example, if a body branch vessel is or becomes offset longitudinally or axially from a pivoting fenestration 12, the pivoting fenestration 12 will pivot the branch vessel prosthesis in the necessary direction and to the necessary degree to maintain the branch vessel prosthesis in place in the branch vessel.

Figure 9:
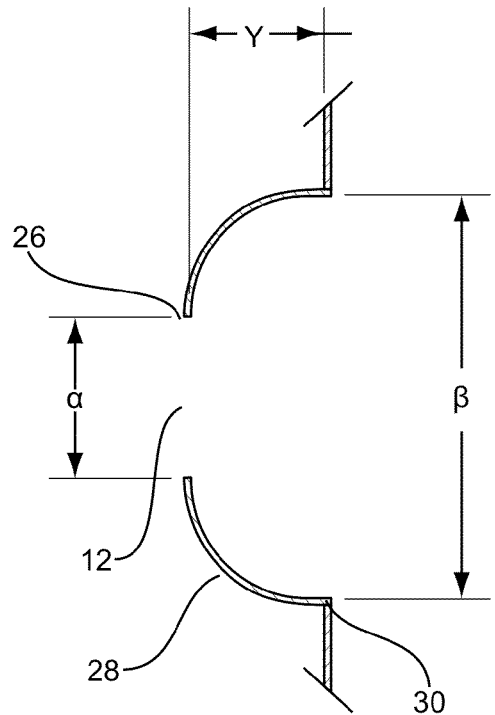
FIG. 9 is a partial, cross-sectional view of a portion of a prosthesis having a pivotable fenestration.

FIG. 9 shows a partial, cross-sectional view of a portion of prosthesis 10 having a pivotable fenestration 12, inner perimeter 26 surrounding fenestration 12, band 28 surrounding inner perimeter 26 and outer perimeter 30 surrounding band 28. The band 28 may be tapered such that the diameter decreases throughout its depth $\gamma$. The depth $\gamma$ may be determined on the amount of movement required for the pivotable fenestration 12 during use and the ability to cannulate the targeted branch vessel. As the depth $\gamma$ decreases, the amount of the second biocompatible material used for the band 28 must also decrease, which limits the range of motion of the pivotable fenestration 12. Furthermore, the depth $\gamma$ must be large enough in order to cannulate the targeted branch vessel. The depth $\gamma$ may range from 3 to 10 mm, and preferably is about 6 mm. As shown, inner perimeter 26 has a diameter $\alpha$ that is smaller than the diameter $\beta$ of outer perimeter 30. The diameter $\alpha$ of the inner perimeter 26 may be determined based on the average size of the targeted branch vessel. In this aspect, the prosthesis 10 may be used to repair a diseased renal artery. Accordingly, the average diameter of the inner perimeter 26 may be based on the average of the diameter of the openings to the renal arteries, or about 6 mm.

The diameter $\beta$ of the outer perimeter 30 may be determined based on the desired amount of movement and the desired patency of the prosthesis 10. As the diameter $\beta$ of the outer perimeter 30 changes, the range of motion also changes. As the diameter $\beta$ of the outer perimeter 30 decreases, the range of motion also decreases. Additionally, the diameter $\beta$ of the outer perimeter 30 must be sized to prevent interference with circumferentially adjacent struts 32, 34 of the stents 16. Hence, the diameter $\beta$ of the outer perimeter 30 may be at most about 15 mm in order to accommodate stents 16. The diameters $\alpha$ and $\beta$ combined with depth $\gamma$ provide the requisite amount of surface area for the pivotable fenestration 12 to pivot during deployment of a secondary branch prosthesis into the fenestration 12 based on dynamic changes to the anatomy.

Figure 10:
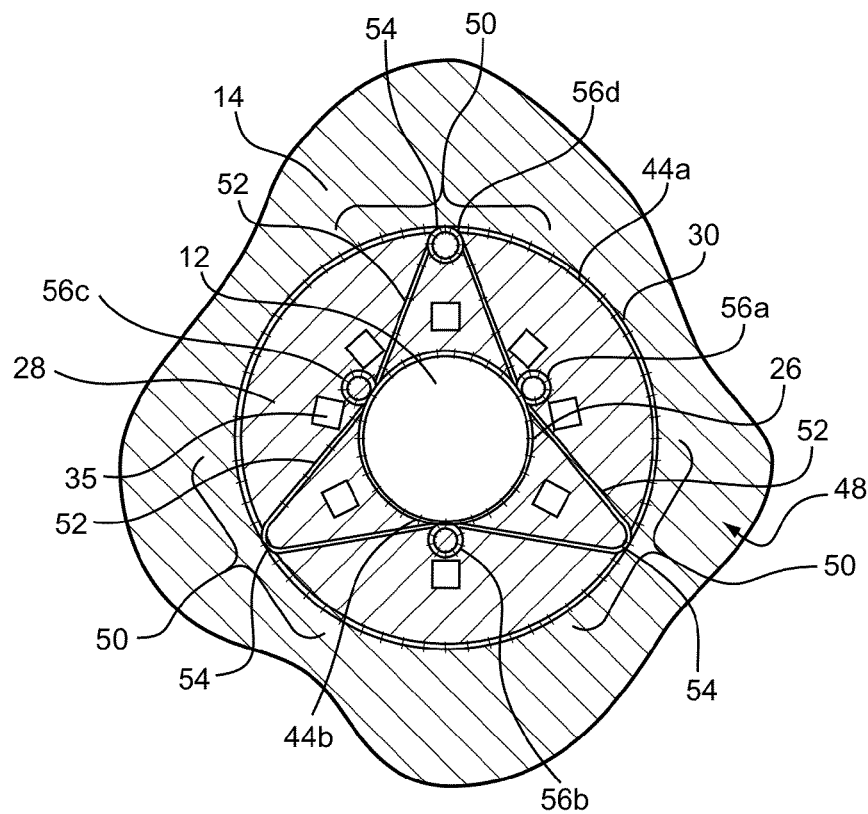
FIG. 10 shows an interior view of a pivotable fenestration where the fenestration is disposed within the lumen of the prosthesis.
Figure 11:
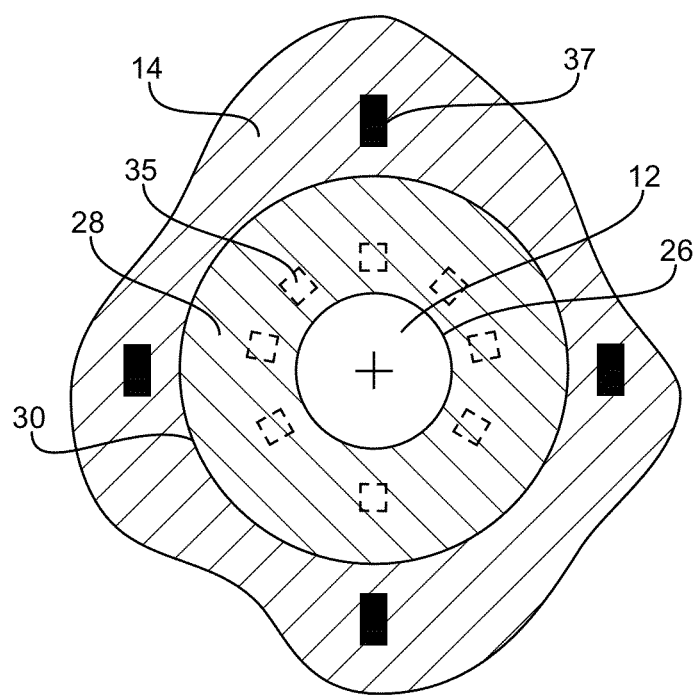
FIG. 11 shows an exterior view of a pivotable fenestration where the fenestration is disposed within the lumen of the prosthesis.

FIGS. 10 and 11 show an internal view and an external view, respectively, of a pivotable fenestration 12 in an aspect where the fenestration is disposed within the lumen 18 of the prosthesis 10. FIG. 10 shows pivotable fenestration 12, inner perimeter 26, band 28, outer perimeter 30. A reinforcement frame 44a is positioned about the outer perimeter 30. A reinforcement frame 44b is positioned about the inner perimeter 26. As discussed above, The reinforcement frames 44a and 44b may be affixed to the outer perimeter 30 and inner perimeter 26 by sewing. Markers 35 are placed around the inner perimeter 26 in order to facilitate proper placement and alignment of a branch vessel prosthesis and the pivotable fenestration 12.

As shown in FIG. 10, the band 28 may be provided with a flexible frame 48. The flexible frame 48 provides support to the band 28 and helps to maintain the overall structure of the band 28 upon deployment within the diseased vessel. The flexible frame 48 also helps to maintain the patency of the pivotable fenestration 12. The flexible frame 48 allows the band 28 of material to reverse orientation and independently move between an interior surface of the prosthesis 10 and an exterior surface of the prosthesis 10 while the device is being deployed. In some embodiments, a physician may alter the orientation of the band 28 during deployment of the prosthesis 10 through the use of endoluminal devices, such as a guidewire catheter. The structure of the flexible frame 48 also prevents the pivotable fenestration 12 from everting or inverting (depending on the initial configuration) once the prosthesis 10 is deployed within the diseased vessel. The flexible frame 48 may be positioned on the band 28 either on the interior or exterior surface of the band 28. In this particular aspect, the flexible frame 48 is positioned on the interior surface of the band 28. The flexible frame 48 comprises a continuous wire formed into a plurality of support units 50 having a generally undulating shape comprising straightened struts 52 interconnected by outwardly facing apices or bends 54. The number of support units 50 may range from about 2 support units to about 10 support units.

In a preferred aspect, the flexible frame 48 has three support units 50. For example, as shown in FIG. 10, the outwardly facing apices 54 may abut or connect to the reinforcing frame 44a of the outer perimeter 30. The outwardly facing apices may be, for example, sewn or sutured to reinforcing frame 44a. The frame 48 may be bent to form a plurality of loops 56a, 56b, 56c, 56d. Loops 56a, 56b, 56c are positioned in the troughs of the apices 54 of adjacent support units 50. Each loop 56a, 56b, 56c may abut or connect to the reinforcing frame 44b of the inner perimeter 26. The loops 56a, 56b, 56c may be, for example, sewn or sutured to reinforcing frame 44b. A loop 56d may be positioned within an apex 54 of a support unit 50. Other aspects may comprise other configurations for the flexible frame 48, including, but not limited to, spirals, may be suitable. The flexible frame 48 may be heat set into the desired configuration prior to attachment to band 28. The flexible frame 48 may be comprised of an elastic or super elastic material, for example and without limitation, nitinol.

FIG. 11 shows an exterior view of a pivotable fenestration 12 where the fenestration is disposed within the lumen 18 of the prosthesis. The pivotable fenestration 12 has an inner perimeter 26 surrounding the fenestration 12, a band 28 surrounding the inner perimeter 26, and an outer perimeter 30 surrounding the band 28. A reinforcement frame 44a is positioned about the outer perimeter 30. Markers 35 may be sewn around the circumference of the outer perimeter 30 in order to facilitate proper placement and alignment of the pivotable fenestration 12 and the targeted branch vessel.

Figure 12:
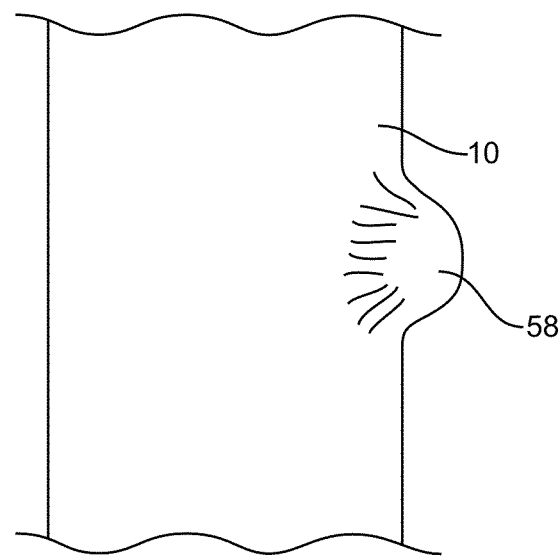
FIG. 12 is a prosthesis having a protrusion of graft material to form a fenestration and an extension.

FIG. 12 shows an embodiment of the band 28 formed from a protrusion 58 having a bubble like configuration as shown in FIG. 12, as described in co-pending U.S. patent application Ser. No. 12/548,120. The protrusion 58 is integrally formed with the body of the prosthesis 10 and is comprised of a second biocompatible graft material. The protrusion 58 may be created during the weaving process used to create the graft material 14. The prosthesis 10 may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). Desirably, the weave comprises a tubular double layer weave. The fabric may be woven on a table loom, a floor loom, a jacquard loom, a counterbalance loom, a jack loom, or an upright loom. Desirably, the fabric is woven on a floor loom. The fabric may have any configuration possible, but preferably has warp and weft yarns. In one aspect, both the warp yarns and the weft yarns are textile yarns.

In order to create the protrusion 58, the number of warp yarns used while weaving the prosthesis 10 is increased in the region where the protrusion 58 is desired. While the additional warp yarns are weaved into the prosthesis 10, the number of weft yarns is kept constant. By increasing the number of warp yarns while holding the number of weft yarns constant, the second biocompatible graft material expands outwardly in the radial direction. The number of warp yarns is increased until a pre-determined diameter has been reached. Once the desired depth for the protrusion 58 is reached, the number of warp yarns introduced into the weaving apparatus is decreased until the number of warp yarns is equal to the number of weft yarns used to form the remainder of the prosthesis 10. A fenestration may be created through the protrusion 58 by applying heat to the center of the protrusion 58. Reinforcing frames may be added about the fenestration 12 and adjacent to and surrounding the protrusion 58 to form the inner and outer perimeters 26, 30 of the prosthesis 10. Further, a flexible frame 48 may be attached to the protrusion 58 to maintain it in its desired extended configuration.

Figure 13:
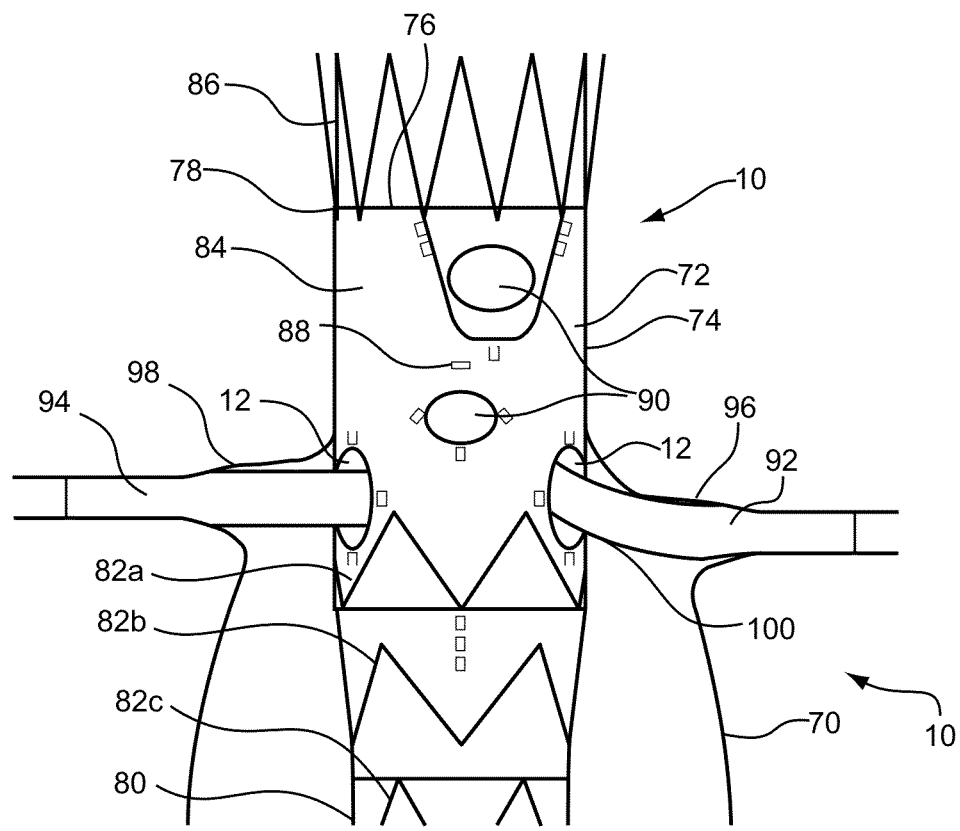
FIG. 13 is a fenestrated prosthesis that has been deployed within a diseased vessel, such as the aorta, where branch vessel prostheses are deployed within the branch vessels.

FIG. 13 depicts an exemplary prosthesis that has been deployed within a diseased vessel 70, such as the aorta. The prosthesis 10 comprises a tubular graft 72 having a sidewall 74 and a lumen 76 disposed longitudinally therein. The prosthesis 10 includes a first end 78 and a second end 80. The tubular graft 72 includes a plurality of rows 82a, 82b, 82c of expandable stents circumferentially aligned affixed to the outer surface 84 of the tubular graft 72. A sealing stent 86 may be affixed to the first end 78 of the tubular graft 72 within the interior surface of the graft 72. The sealing stent 86 may be attached to the first end 78 of the tubular graft 72 by any attaching mechanism, for example and without limitation, suturing. Radiopaque markers 88 may be placed on the tubular graft 72 in order to assist with proper alignment of the tubular graft 72 when deployed within a patient. Fenestration 90 may be disposed through the tubular graft 72. The distal end (not shown) of the prosthesis 10 may be bifurcated.

The tubular graft 72 also includes two internal pivotable fenestrations 12 that are in communication with the lumen 76. The tubular graft 72 may be preloaded onto a delivery device for deployment within a patient. The delivery device includes a sheath over the tubular graft 72 to keep the tubular graft 72 in a compressed state prior to deployment. The delivery device is placed over a guide wire and after checking the appearance and orientation of the device under x-ray, guide wires for each fenestration 12 are loaded through side ports in the handle of the delivery device. The delivery device is introduced over the guide wire, and advanced until a tapered tip of the delivery device is in the femoral artery and the radiopaque markers 88 indicating the fenestrations 12 are at a level of the appropriate arteries. A sheath is advanced over the guide wire for each fenestration 12 through each side port on the handle of the device. Once the sheaths for the fenestrations 12 are in position, the tubular graft 72 can be advanced to its correct position and orientation for deployment. The tubular graft 72 is deployed by withdrawing the sheath covering the graft 72 over the pusher. The operator can perform angiography and adjust the placement of the tubular graft 72 if necessary. Deployment is continued until the tubular graft 72 is fully unsheathed. The sheaths for the fenestrations 12 are advanced over the wires until they are at a level of the lower margin of the fenestration 12. The sheaths for the fenestrations 12 are punctured and a guide wire is advanced through each sheath. A catheter is advanced over the guide wires, and once the catheters are in the target vessels, a stiffer wire replaces the guide wire. The sheaths for the fenestrations 12 are then advanced into the target vessels and branch vessel prostheses are advanced through the sheath and placed in the desired position.

FIG. 13 illustrates in accordance with the procedure described above branch vessel prosthesis deployed through each of the two fenestrations 12. Branch vessel prostheses 92, 94 are formed from biocompatible materials and may comprise covered stents. Alternatively, they may comprise bare stents. The covered or bare stents may be either self-expanding or balloon expandable. In one aspect the branch vessel stent may have both self-expanding and balloon expandable components. For example, the branch vessel stent may have an end not shown for placement within the fenestration 12, and thus upon deployment, may be either self-expanding or by balloon expanding. If the branch vessel stent is a covered stent, the graft material used may comprise one or more of the biocompatible materials are discussed above.

As shown in FIG. 13, the branch vessel prostheses 92, 94 are deployed into branch vessels 96, 98 such as the right and left renal arteries. As shown in FIG. 13, the right opening 100 is not completely aligned with the right branch vessel 96. Particularly, the right branch vessel 96 is positioned lower than the corresponding left branch vessel 98. To accommodate placement of the branch vessel prosthesis 92 into the right branch vessel 96, the pivotable fenestration 12 provides the requisite flexibility and ability to pivot required for the branch vessel prosthesis 92 to deploy into the desired position.

Figure 14:
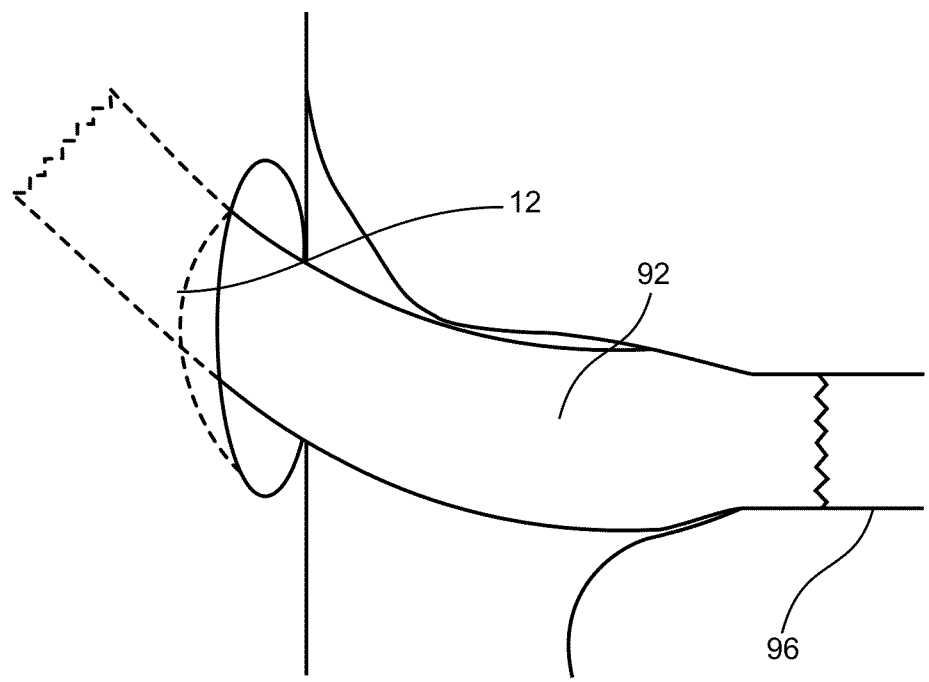
FIG. 14 shows a branch vessel prosthesis deployed in a secondary branch vessel, where the branch vessel prosthesis is deployed in a right branch vessel positioned lower than its corresponding left branch vessel.
Figure 15:
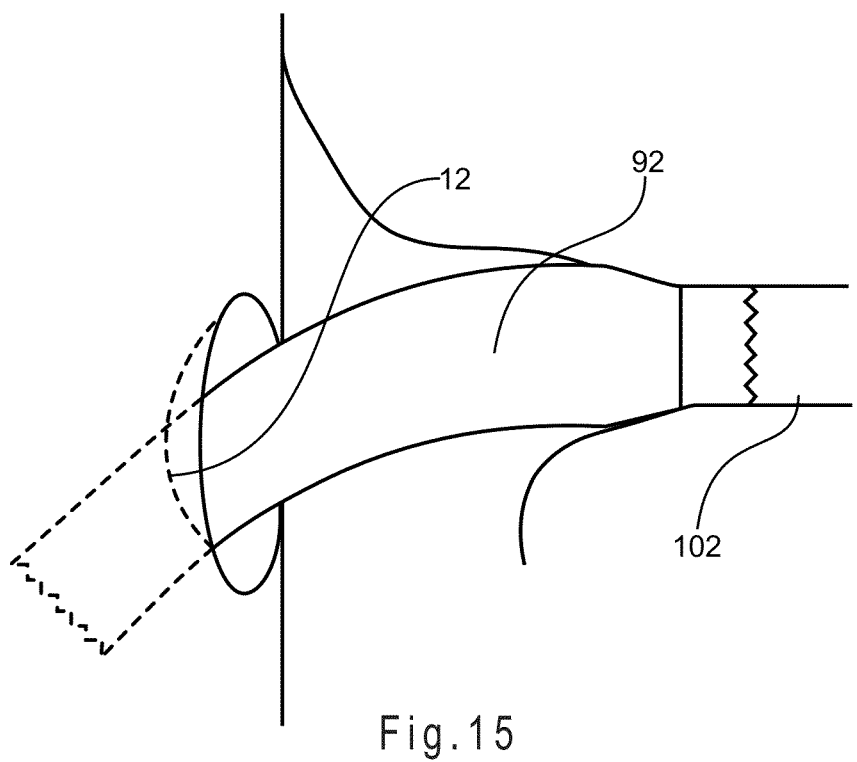
FIG. 15 shows a branch vessel prosthesis deployed in a secondary branch vessel, where the branch vessel prosthesis is deployed in a right branch vessel positioned higher than its corresponding left branch vessel.

FIGS. 14 and 15 show a branch vessel prosthesis 92 deployed in a secondary branch vessel in greater detail. As shown in FIG. 14, the branch vessel prosthesis 92 is deployed within the right branch vessel 96, which is positioned lower than its corresponding left branch vessel 98. Alternatively, as shown in FIG. 15, the branch vessel prosthesis 92 is deployed within the right branch vessel 102, which is positioned higher than its corresponding left branch vessel. The pivotable fenestration 12 allows for pivoting motion to accommodate the offset position of the right branch vessel 96, 102 and provide access to the right branch vessel 96, 102 through the use of a delivery device, such as a catheter.

Once a catheter is placed within right branch vessel 96, 102, the branch vessel prosthesis 92 may be deployed within the right branch vessel 96, 102. The branch vessel prosthesis 92 may be balloon expandable or self-expandable. In this aspect, the branch vessel prosthesis 92 is balloon expandable. Once the secondary branch prosthesis 146 is deployed in the right branch vessel 96, 102, the end of the branch vessel prosthesis 92 remaining within the interior surface of the prosthesis 10 may be flared in order to provide a proper seal between the fenestration 12 and the right branch vessel 96, 102.

Figure 16:
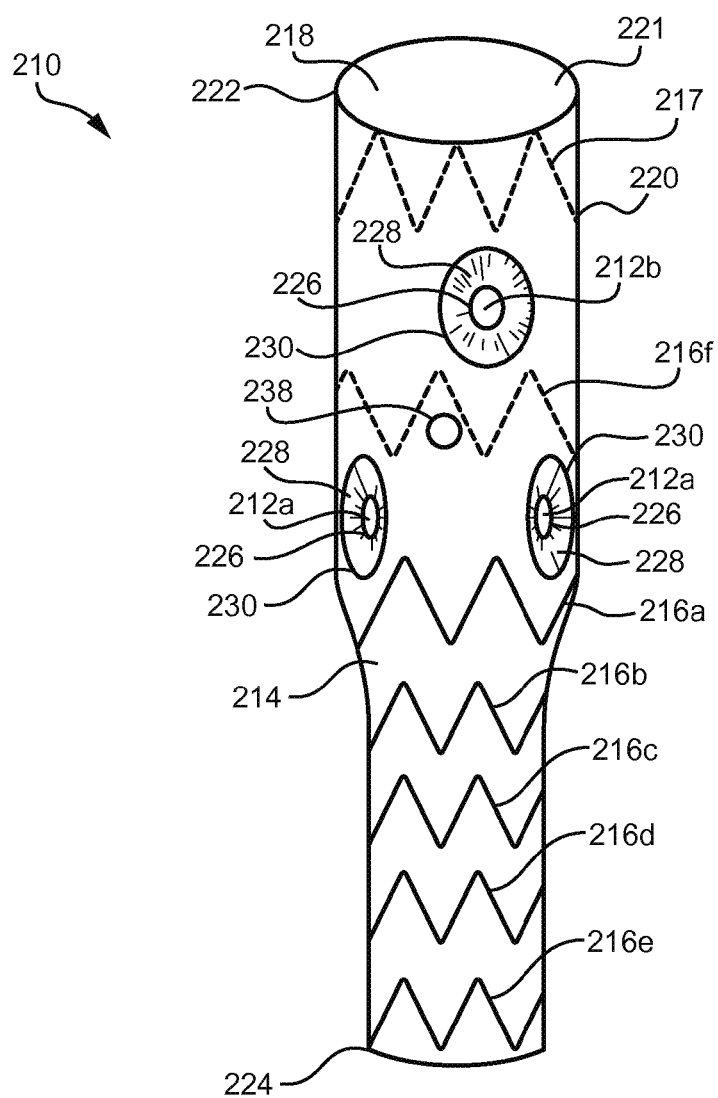
FIG. 16 shows an alternative fenestrated prosthesis having pivoting fenestrations.

FIG. 16 shows alternative aspects of a prosthesis 210. FIG. 16 shows a prosthesis 210 that is a stent graft. The prosthesis 210 includes graft material 214 associated with one or more stents 216. The prosthesis 210 has a proximal end 222, a distal end 224, and a lumen 218 extending through the prosthesis 210. The stents 216 may be placed on the external surface 220 and/or internal surface 221 of the graft material 214. In some embodiments, the stents may all be placed on the external surface 220 of the graft material 214. In one particular embodiment, the prosthesis 210, such as that shown in FIG. 16, has external body stents 216a, 216b, 216c, 216d, 216e and at least one internal stent 216f. The stents 216a, 216b, 216c, 216d, and 216e are positioned longitudinally adjacent to each other and the apices of each row are in circumferential alignment, or "in phase", with the apices of longitudinally adjacent rows. The prosthesis 210 may also include a sealing stent 217 positioned at the proximal end 222 of the prosthesis 210 to seal the prosthesis 210 at the proximal end 222 to the walls of the blood vessel into which it has been placed. In alternative embodiments, depending on the location of the prosthesis 210 or a particular need, a sealing stent 217 may be placed at either or both the proximal and distal ends 222, 224 of prosthesis 210. As shown in FIG. 16, the internal stent 216f is positioned "out of phase" by about 180 degrees with longitudinally adjacent row 216a, such that circumferentially about the surface of the graft, every other apex of the internal stent 216f matches with every other apex of stent row 216a. In other embodiments, the internal stent 216d may be positioned in phase with longitudinally adjacent row 216a, or the internal stent 216d may be out of phase by an amount less than 180 degrees. The prosthesis 210 also may include an attachment mechanism, for example, an attachment stent, at either or both ends 222, 224 of the prosthesis 210, to further secure the prosthesis 210 within the body vessel and prevent migration of the prosthesis 210.

The prosthesis 210 has several openings or fenestrations 212, 238 that extend from an internal surface 221 to the external surface 220 of the graft material 214. The prosthesis 210 of FIG. 16 has two renal pivotable fenestrations 212a, a celiac pivotable fenestration 212b, and a superior mesenteric artery non-pivotable fenestration 238. In other embodiments, the prosthesis 210 may include all pivotable fenestrations 212 that extend from an internal surface 221 to the external surface 220. Pivotable fenestrations 212 have a first, inner perimeter 226 surrounding the fenestration 212, a band of material 228 surrounding the inner perimeter 226, and a second, outer perimeter 230 surrounding the band 228. The inner perimeter 226, the band 228 and the outer perimeter 230 would be substantially concentric with one another if they were in the same plane, for example the surface plane of the graft. The inner perimeter 226, the band 228 and the outer perimeter 230 may form a geometric shape. In an exemplary embodiment, the inner perimeter 226, the band 228 and the outer perimeter 230 may form a hemispherical shape, resembling a dome. In alternative aspects, other geometric shapes, including, but not limited to, a frustoconical cone extending from the surface of the graft material 214, may be used with alternative embodiments. The pivoting fenestrations 212a may be positioned between opposing struts of longitudinally adjacent stent rows 216f and 216a. The diameter of the inner perimeter 226 may be determined based on the average size of the targeted branch vessel. In this aspect, the diameter of the inner perimeter 226 of pivotable fenestration 212a may be based on the average of the diameter of the openings to the renal arteries, or about 6 mm. Furthermore, the diameter of the inner perimeter 226 of pivotable fenestration 212b may be based on the average of the opening of the celiac artery, or about 8 mm. The diameter of the non-pivotable fenestration 238 may be based on the average of the opening of the superior mesenteric artery, or about 8 mm.

The inner perimeter 226, the band 228, and the outer perimeter 230 may be integral with the graft material 214 or attached separately to the graft material 214. The band 228 may be comprised of the same or different biocompatible material as the graft material 214. For example, the biocompatible material forming the band 228 may have greater pliability than the biocompatible graft material used for the tubular graft body. The band 228 is sufficiently flexible to permit the fenestration 212a, 212b to move such that a branch stent disposed in the fenestration 212a, 212b may be oriented upwardly, downwardly, laterally, diagonally and the like. Furthermore, the band 228 of material may move independently between an interior surface 221 of the prosthesis 210 and an exterior surface 220 of the prosthesis 210 while the device is being deployed. In some embodiments, the band 228 may be able to move up to 6 mm while the device is being deployed within a patient. In alternative embodiments, a flexible frame may be disposed on a surface of the band 228. The depth of the band 228 may extend within the interior surface 221 of the prosthesis 210 or outward from the exterior surface 220 of the prosthesis 210. The depth may be determined based on the amount of movement required for the pivotable fenestrations 212a, 212b during use and the ability to cannulate the targeted branch vessel.

The pivotable fenestrations 212a, 212b allow the prosthesis 210 to be used with a variety of patients, due to its ability to adapt to the variance in the positioning of the branch vessels. For example, if a body branch vessel is or becomes offset longitudinally or axially from a pivoting fenestration 212, the pivoting fenestration 212 will pivot the branch vessel prosthesis in the necessary direction and to the necessary degree to maintain the branch vessel prosthesis in place in the branch vessel. This embodiment of the prosthesis 212 may be useful in treating Type IV thoracoabdominal aortic aneurysms that involve all four visceral branch arteries (celiac, superior mesenteric artery, and the renal arteries). In these aneurysms, the disease expands above superior mesenteric artery, and it may necessary to position a stent graft into the thoracoabdominal aorta, which could occlude these vessels. Accordingly, pivotable fenestrations 212a, 212b allow for variation in placing the graft within a patient, while allowing for the flow of blood to continue into these arteries.

Figure 17:
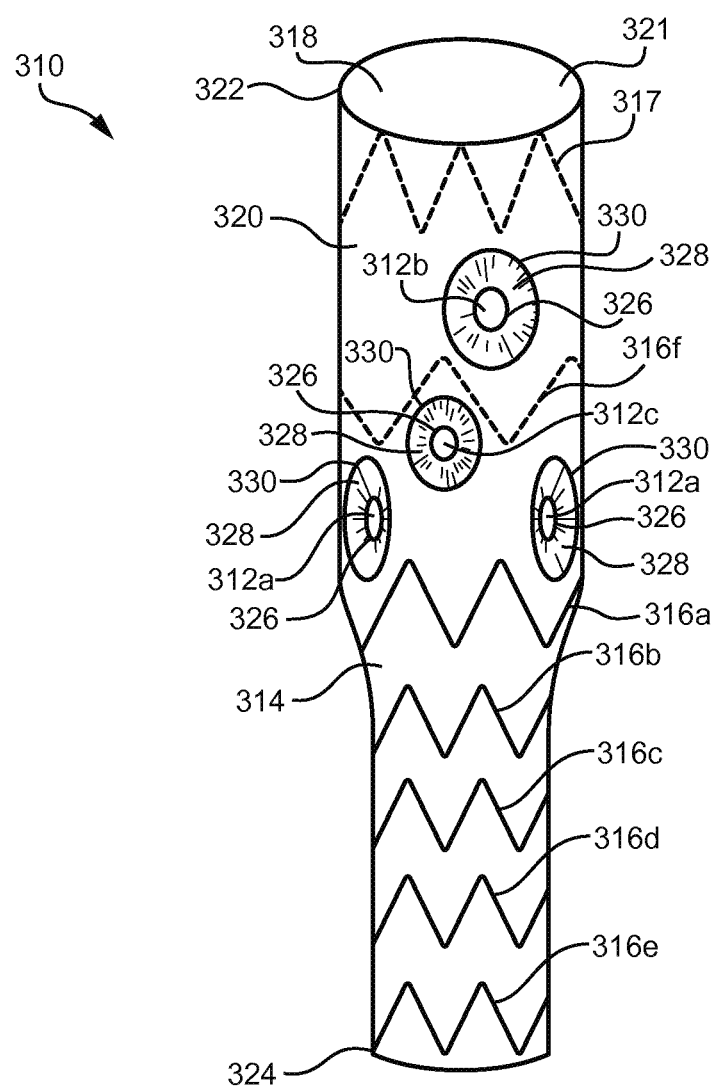
FIG. 17 shows an alternative embodiment of a prosthesis having a pivotable fenestration.

FIG. 17 shows an alternative embodiment of a prosthesis 310. The prosthesis 310 includes graft material 314 associated with one or more stents 316, having a proximal end 322, a distal end 324, and a lumen 318 extending therethrough. The prosthesis 310, such as that shown in FIG. 16, has external body stents 316a, 316b, 316c, 316d, 316e and at least one internal stent 316f. The stents 316a, 316b, 316c, 316d, 316e are positioned longitudinally adjacent to each other and the apices of each row are in circumferential alignment, or "in phase", with the apices of longitudinally adjacent rows. The internal stent 316f is positioned "out of phase" by about 180 degrees with longitudinally adjacent row 316a, such that circumferentially about the surface of the graft, every other apex of the internal stent 316f matches with every other apex of stent row 316a. A sealing stent 317 is positioned at the proximal end 322 of the prosthesis 310 to seal the prosthesis 310 at the proximal end 322 to the walls of the blood vessel into which it has been placed.

The prosthesis 310 has several openings or fenestrations 312 that extend from an internal surface 321 to the external surface 320 of the graft material 314. The prosthesis 310 of FIG. 17 has two renal pivotable fenestrations 312a, a celiac pivotable fenestration 312b, and a superior mesenteric artery pivotable fenestration 312c. Pivotable fenestrations 312a, 312b, 312c have a first, inner perimeter 226 surrounding the fenestration 312, a band of material 228 surrounding the inner perimeter 326, and a second, outer perimeter 330 surrounding the band 328. The inner perimeter 326, the band 328 and the outer perimeter 330 would be substantially concentric with one another if they were in the same plane, for example the surface plane of the graft. The inner perimeter 326, the band 328 and the outer perimeter 330 form a hemispherical shape. The diameter of the inner perimeter 326 may be determined based on the average size of the targeted branch vessel. In this aspect, the diameter of the inner perimeter 326 of pivotable fenestration 312a may be based on the average of the diameter of the openings to the renal arteries, or about 6 mm.

Furthermore, the diameter of the inner perimeter 326 of pivotable fenestration 312b may be based on the average of the opening of the celiac artery, or about 8 mm. The diameter of the fenestration 312c may be based on the average of the opening of the superior mesenteric artery, or about 8 mm.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. An endoluminal prosthesis, comprising:
   a graft having a tubular body and a surface comprising a first biocompatible material;
   a stent frame having a plurality of stent units attached to the graft about the surface of the graft and arranged in longitudinally spaced rows, at least one of the stent units comprising a plurality of struts interconnected by apices;
   at least three fenestrations disposed through a sidewall of the graft, each fenestration having a diameter;
   a first perimeter having a first diameter and surrounding each of the fenestrations;
   each first perimeter having a band of flexible material attached to and surrounding the perimeter, the band of flexible material having a depth relative to a surface plane of the tubular body; and
   each band of flexible material having a second perimeter attached to and surrounding the band of flexible material;
   where the first perimeters, the bands of flexible material, and the second perimeters have a geometric shape,
   where each fenestration is pivotable in any direction away from an axis perpendicular to a longitudinal axis of the prosthesis, and
   where at least two of the fenestrations are positioned on opposing sides of the graft, where the first perimeter, the band of material, and the second perimeter of at least one of the at least three fenestrations has a hemispherical shape.

2. The prosthesis of claim 1, where the first perimeter of at least one of the fenestrations has a diameter of about 8 mm.

3. The prosthesis of claim 1, where the first perimeter of at least two of the fenestrations has a diameter of about 6 mm.

4. The prosthesis of claim 1, where the band of flexible material is separately attached to the surface of the graft.

5. The prosthesis of claim 1, where the band of flexible material is integral with the sidewall of the graft.

6. The prosthesis of claim 1, further comprising a frame attached to and surrounding the second perimeter.

7. The prosthesis of claim 1, wherein the band of flexible material surrounding at least one of the fenestrations has a concave or convex orientation relative to the surface of the graft.

8. The prosthesis of claim 1, where the band of flexible material surrounding at least one of the fenestrations has a depth that ranges from about 3 mm to about 10 mm.

9. The prosthesis of claim 1, wherein at least one of the fenestrations is configured to be positioned about the celiac artery.

10. A prosthesis for treatment of a main vessel defect near one or more branch vessels, comprising:
    a graft having a surface comprising a biocompatible material;
    a stent frame having a plurality of stent units attached to the graft about the surface of the graft and arranged in longitudinally spaced rows, at least one of the stent units comprising a plurality of struts interconnected by apices;
    a plurality of fenestrations disposed through a sidewall of the graft, each having a diameter;
    a first perimeter having a first diameter and surrounding each of the fenestrations;
    each first perimeter having a band of material attached to and surrounding the perimeter;
    each band of material having a second perimeter attached to and surrounding the band of material;
    where the first perimeters, the bands of material, and the second perimeters have a hemispherical shape,
    where each fenestration is pivotable in any direction away from an axis perpendicular to a longitudinal axis of the prosthesis and where the diameter of the first perimeter attached to and surrounding at least one of the fenestrations is about 8 mm.

11. The prosthesis of claim 10, where the band of material is separately attached to the surface of the graft.

12. The prosthesis of claim 10, where the band of material is integral with the sidewall of the graft.

13. The prosthesis of claim 10, wherein the band of material has a concave or convex orientation relative to the surface of the graft.

14. The prosthesis of claim 10, wherein at least one of the fenestrations is configured to be positioned proximate the superior mesenteric artery.

15. The prosthesis of claim 10, wherein at least one of the fenestrations is configured to be positioned proximate the celiac artery.

16. The prosthesis of claim 10, further comprising a frame attached to and surrounding the second perimeter.

17. An endoluminal prosthesis, comprising:
    a graft having a tubular body and a surface comprising a first biocompatible material;
    a stent frame having a plurality of stent units attached to the graft about the surface of the graft and arranged in longitudinally spaced rows, at least one of the stent units comprising a plurality of struts interconnected by apices;
    four fenestrations disposed through a sidewall of the graft, each having a diameter;
    a first perimeter having a first diameter and surrounding each of the fenestrations;
    each first perimeter having a band of flexible material attached to and surrounding the perimeter, the band of flexible material having a depth relative to a surface plane of the tubular body; and
    each band of flexible material having a second perimeter attached to and surrounding the band of flexible material;
    where each fenestration is pivotable in any direction away from an axis perpendicular to a longitudinal axis of the prosthesis and at least one of the fenestrations is configured to be positioned proximate to the celiac artery, and where the first perimeter, the band of material, and the second perimeter of at least one of the four fenestrations has a hemispherical shape.

18. The prosthesis of claim 17, where the first perimeter attached to and surrounding at least one of the fenestrations has a diameter of about 8 mm.

19. The prosthesis of claim 17, wherein the band of flexible material has a concave or convex orientation relative to the surface of the graft.

20. The prosthesis of claim 17, where the band of flexible material is separately attached to the surface of the graft.

21. The prosthesis of claim 17, where the band of flexible material is integral with the sidewall of the graft.

22. The prosthesis of claim 17, further comprising a frame attached to and surrounding the second perimeter.

* * * * *